United States Patent [19]
Mandelkern

[11] Patent Number: 5,133,752
[45] Date of Patent: Jul. 28, 1992

[54] LAUNDERABLE PROSTHETIC DEVICE

[76] Inventor: Isabel Mandelkern, 8833 W. 75th St., Overland Park, Kans. 66212

[21] Appl. No.: 483,445

[22] Filed: Feb. 22, 1990

[51] Int. Cl.$^5$ .............................................. A61F 2/52
[52] U.S. Cl. .......................................... 623/7; 623/8
[58] Field of Search ...................................... 623/7-8; 128/90-95, 96, 97, 78, 95.1

[56] References Cited

U.S. PATENT DOCUMENTS

| | | |
|---|---|---|
| Re. 26,790 | 2/1970 | Silverman . |
| 2,066,503 | 1/1937 | Wiggers ................................. 623/7 |
| 2,222,488 | 11/1940 | Rich .................................... 128/96.1 |
| 2,501,903 | 3/1950 | Huggins . |
| 2,814,808 | 12/1957 | Berman ................................. 623/7 |
| 3,189,921 | 6/1965 | Pangman ............................... 623/8 |
| 3,278,947 | 10/1966 | Silverman . |
| 3,348,241 | 10/1967 | Dodds ................................. 623/7 |
| 3,526,221 | 9/1970 | Garber ............................... 128/95.1 |
| 3,623,488 | 11/1971 | Nakayama .......................... 128/95.1 |
| 3,795,921 | 3/1974 | Zucker . |
| 4,019,209 | 4/1977 | Spence ................................ 450/55 |
| 4,627,109 | 12/1986 | Carabelli et al. ..................... 128/78 |
| 4,772,281 | 9/1988 | Armstead ........................... 604/358 |
| 4,828,559 | 5/1989 | Greenberg . |
| 37845,507 | 11/1974 | Kirby et al. . |

Primary Examiner—David Isabella
Assistant Examiner—G. Gualtieri
Attorney, Agent, or Firm—Litman, McMahon & Brown

[57] ABSTRACT

A launderable prosthetic device for camouflaging missing or deformed human body mass or parts comprises a plurality of layers which are sized, shaped and interconnected to form a composite structure that, when partially compressed, assimilates the size, shape and resiliency of the camouflaged body mass. A soft inner liner provides an interface between the composite structure and the human body surface and a smooth outer shield liner provides an interface between the composite structure and an abutting outer garment. The liners are joined to enclose the composite structure and cooperate to maintain the composite structure in a partially compressed state. Randomly spaced openings in the layers provide ventilation for the body surface abutting the prosthetic device. In one embodiment of the device, the layers are progressively sized laterally larger and opposite sides of each of the layers are joined to respective sides of the other layers so as to form a bowed construction adapted to fit a curved surface of a user.

15 Claims, 3 Drawing Sheets

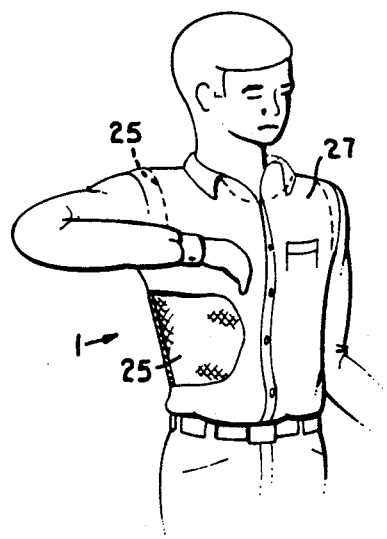
Fig. 1.
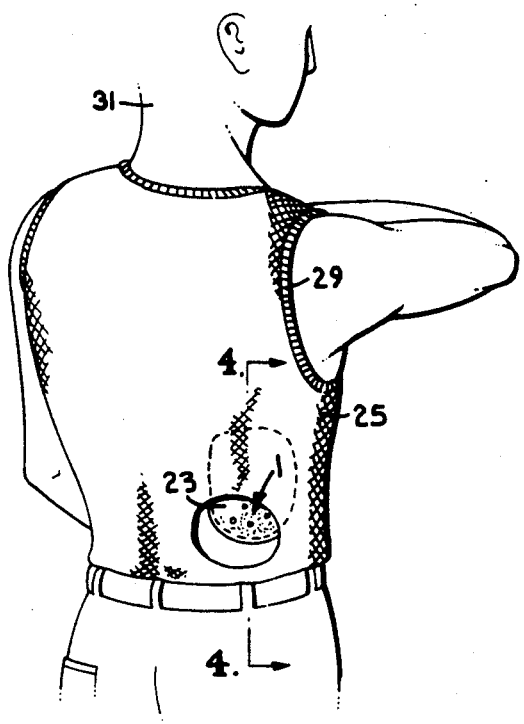
Fig. 2.
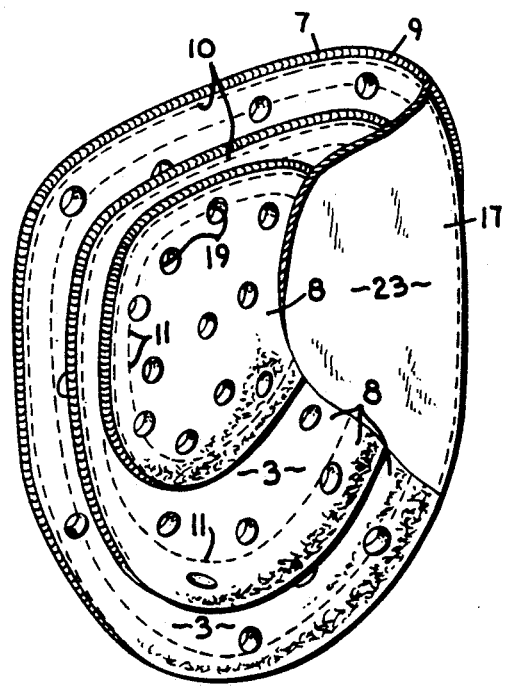
Fig. 3.
Fig. 4.

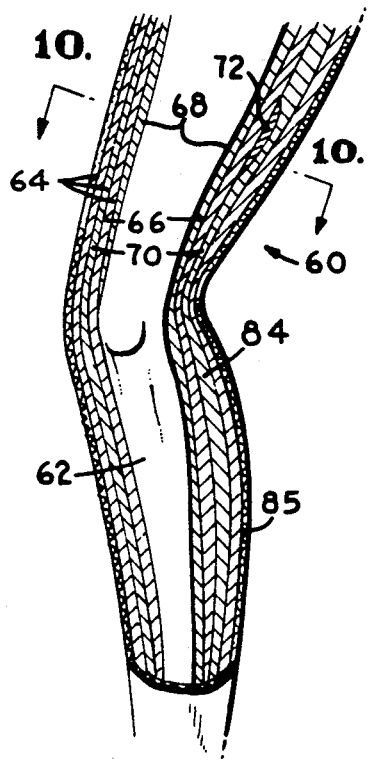
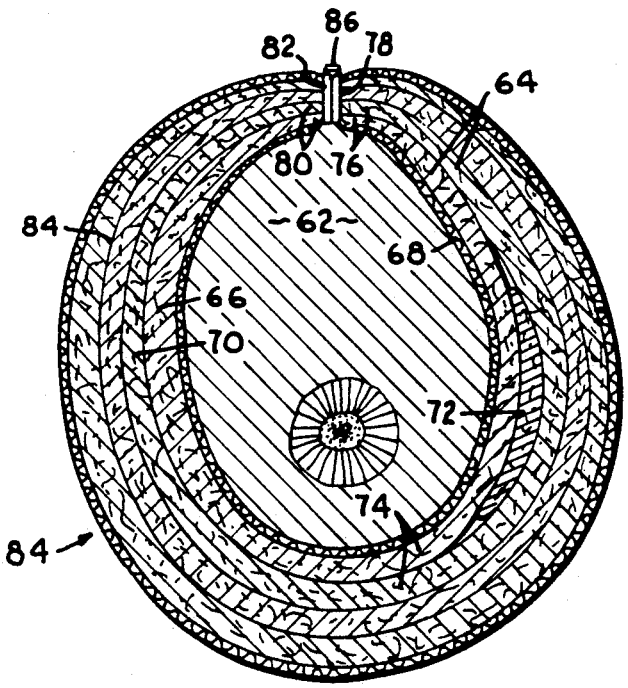
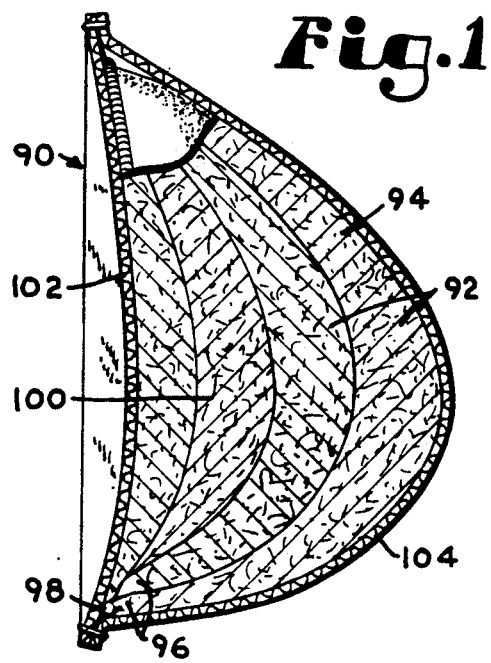
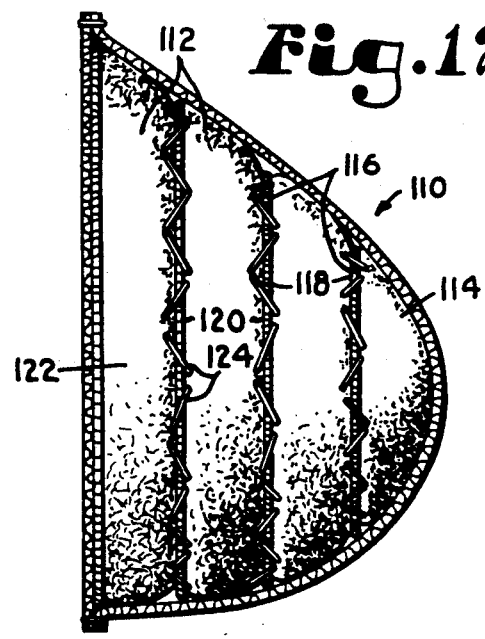

LAUNDERABLE PROSTHETIC DEVICE

FIELD OF THE INVENTION

The present invention relates to a prosthesis for correcting a deficiency in a human body profile resulting from deformed or missing body mass or parts.

BACKGROUND OF THE INVENTION

Disease, accidents, birth defects, battlefield injuries and a variety of other incidents cause human bodies to become disfigured or distorted. In many of those situations, the victim's body may still be able to function physically to a greater or lesser degree. However, many times the victim thereof suffers severe physiological and psychological trauma associated therewith due to perceived inferiority relative to surrounding members of society resulting from the real or imagined obviousness of the deformity.

The trauma is generally reinforced on a daily basis when the victim dons his or her attire only to be reminded of the unnatural draping of the clothing in the proximity of the missing or distorted body mass. In an attempt to compensate for the perceived inferiority, the victim sometimes physically responds in a manner which might tend to conceal or camouflage the disfigurement. For example, a female victim may tend to hunch her shoulders toward the site of a mastectomy surgery.

In order to alleviate the trauma that results from such missing or distorted human body mass, a variety of prosthetic devices have been utilized in an attempt to minimize the obvious anomaly associated therewith.

One approach has been to form a single lump of resilient material which approximates the original size, shape and weight of the missing body mass. Usually, some type of harness is then used to secure and confine the prosthesis to the proximity of the deformity. Unfortunately, such a lump of resilient material is generally impervious to air flow and, as a result, is not conducive to ventilation of the surface of skin covered by the prosthesis or for conveying away body moisture that may accumulate between the lump and the underlying body surfaces. For this and other reasons, such devices are often uncomfortable to wear.

Further, the mass of the single lump of material has certain inertial properties of its own which are separate and apart from those of the body structure located nearby. As a result, the prosthesis may begin to work loose, flop or bounce when the victim ambulates, or may otherwise become disoriented relative to the deformity which it was designed to conceal. Then, instead of enjoying the psychological security desired, the victim may experience further embarrassment because, not only is the deformity then apparent, but the unsuccessful attempt to cover the defect has been exposed by the obvious presence of the misplaced artifice.

Finally, this type of prosthesis is not usually adapted for frequent subjection to normal and customary cleaning and laundering practices for periodic sanitation maintenance purposes.

Another approach sometimes used to try to camouflage a missing or deformed body mass has been to form layers of materials to reconstruct the missing body profile and resilience characteristics, some of which attempts include inflatable pockets for in situ adjustment of size and shape. Although some of these devices do provide a lighter, more comfortable prosthesis, many still retain and exhibit the same undesirable characteristics discussed above, particularly with regard to discomfort caused by accumulated body moisture and misalignment of the prosthesis with other normal body profile lines during physical activity.

It is further noted that such devices are either constructed of pieces that are not interconnected in which case the pieces are displaced during laundering or the like so that the device loses its shape or alternatively are interconnected by tight stitching or the like that prevents movement of one piece relative to another such that the prosthesis appears very stiff and unnatural.

Most of the prior art devices are deficient in providing a complete profile correction of the missing or deformed body mass, expensive to purchase, difficult to maintain, difficult to put on and take off (especially where the prosthesis must encircle a body part), and incapable of frequent exposure to conventional cleaning or laundering environments.

SUMMARY OF THE INVENTION

An improved launderable prosthesis is provided to fill out and correct the profile lines of a human wearer having a surface deformity of the body and thereby camouflage and conceal the existence of the same. The prosthesis comprises a plurality of polyester fiber layers or pads, each of which has been reinforced by stitching along the peripheral edge thereof. The layers are each individually dimensioned such that when the layers are spaced in face-to-face abutment, the composite size and shape of the multiple pads acting in unison assimilate the size and shape of the deformity sought to be concealed.

Preferably, the pads are constructed of polyester fiber which is very durable and which is readily subjectable to conventional laundering and cleaning procedures. Costwise, polyester fiber is readily available and relatively inexpensive.

An important feature of the prosthesis is the interconnecting securement of the various pads to each other. The face of each pad, in an area inset from the peripheral edge thereof, is stitched to the face of each adjacent abutting pad. Except for the special applications as hereinafter provided, it is important that the interconnecting stitches not pass completely through each pad but, instead, are confined to the material in the proximity of the abutting faces of the respective pads. In this manner, the peripheral edges of the various pads comprising the composite prosthesis, as well as each entire pad to a lesser extent, can "work" relative to each other and thereby more closely assimilate the normal resiliency and relational movement of the absent body mass. That is, such "tacking" of the layers together gives a very realistic appearance to the prosthesis that moves and stretches with the surrounding body tissue rather than having a very solid and lumpy appearance as do many prostheses.

For those applications which require a greater throughput of body moisture transference, randomly spaced openings or bores are cut into the inner pads of the composite structure of the prosthesis to enhance ventilation characteristics of the prosthesis. The dimensions of the openings depend largely on the thickness and lateral size of the pads. If greater ventilation is desired, larger openings are provided. An unexpected benefit of the openings through the inner pads is the thermally insulating characteristics which are realized as a result of the openings also serving as dead-air spaces.

A layer of relatively soft, non-abrasive fabric is placed between the inside face of the innermost layer of polyester fiber and the abutting human body surface. Likewise, preferably another layer of skin-colored fabric is utilized to cover the outer exposed surfaces of the polyester fiber layers and the outer fabric layers are joined together by sewing or the like to form a completely containing enclosure for the polyester layers.

For those applications which require a profile with a curved, protruding, convex surface, one or more outer pads or layers are constructed having greater lateral dimensions than the layers situated closer to the wearer's body. Then, the peripheral edges of the pads or layers are gathered and secured together. As a result, the composite configuration bulges toward the layers having the larger dimensions, thereby providing the desired convex contouring. The greater the progressive difference in dimensions in the outwardly spaced layers, the greater the resulting curvature. Fasteners, such as a zipper, can be used to connect the opposite ends of the layer when the device is used to completely encircle a body part such as a leg.

Various methods can be utilized for securing the completed prosthesis in place; the particular method depends on the area of the body of the wearer which will receive the prosthesis. For some applications, a band or strip of one part of a hook and loop fastener, (such as that marketed under the trade name Velcro), can be attached to clothing or the like and the opposite part can be secured to the prosthesis for securing the prosthesis in a desired location. For other applications, particularly in the upper torso area, a jacket or vest made of relatively non-elastic, porous material can be worn by the user with the prosthesis secured to an inner surface thereof (such as by pinning, stitching, or the like). For yet other applications, the prosthesis may be appropriately pinned to or placed in an undergarment, such as a breast prosthesis positioned in a brassiere.

OBJECTS OF THE INVENTION

Therefore, the objects of the present invention are: to provide a device and a method to compensate for a deficient human body profile caused by missing or deformed body parts or mass; to provide such a device that includes independently movable layers lightly stitched together or otherwise interconnected to prevent disarray of the layers but to also allow the layers, especially the edges thereof, some degree of relative movement to provide a more natural appearance to those seeing the user of the device; to provide such a device which causes clothing associated therewith to maintain a normal appearance when a wearer assumes a multiplicity of positions such as lying down, standing up, leaning over, bending to the side, etc.; to provide such a device utilizing materials and methods of construction which permit ordinary and customary laundering and cleaning procedures; to provide such a device which yields psychological reassurance to the wearer that beholders will not be alerted to the existence of the missing body part or mass; to provide such a device which is comfortable to wear; to provide such a device which promotes diffusion of accumulated body moisture away from the body; to provide such a device which exhibits thermally insulating qualities; to provide a device which assimilates the shape, size, firmness, and various other qualities of the missing human body part or mass; and to generally provide such a device which is relatively easy to don and remove, simple to maintain, reliable in performance, inexpensive to manufacture, and which generally performs the requirements of its intended purposes.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of the upper torso of a wearer utilizing a launderable prosthetic device in accordance with the present invention.

FIG. 2 is a rear perspective view of the upper torso of the wearer utilizing the profile prosthetic device with a portion cut away to reveal details thereof.

FIG. 3 is an enlarged plan view of the prosthetic device with portions cut away to reveal details of layers therein.

FIG. 4 is a fragmentary and enlarged cross-sectional view of the wearer and the prosthetic device, taken along line 4—4 of FIG. 2.

FIG. 9 is a perspective view of a leg of a user and a second modified embodiment of a launderable prosthetic device, partially broken away to show interior detail thereof, for the leg in accordance with the present invention.

FIG. 10 is an enlarged, cross-sectional view of the leg and the second modified prosthetic device, taken along line 10—10 of FIG. 9.

FIG. 11 is a cross-sectional view of a third modified embodiment of a launderable prosthetic device for replacing a missing breast of a wearer in accordance with the present invention.

FIG. 12 is a cross-sectional view of a fourth modified embodiment of a launderable prosthetic device for replacing a breast of a wearer in accordance with the present invention.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 5:
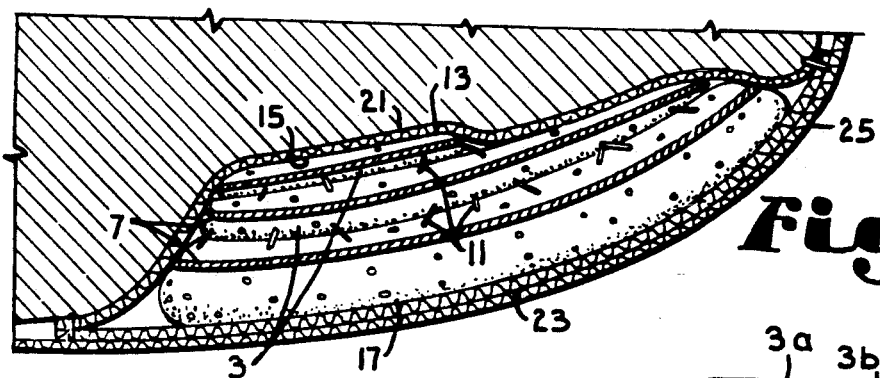
FIG. 5 is a fragmentary and enlarged cross-sectional view of the wearer and the prosthetic device, taken along line 5—5 of FIG. 4, with portions cut away to show details thereof.
Figure 6:
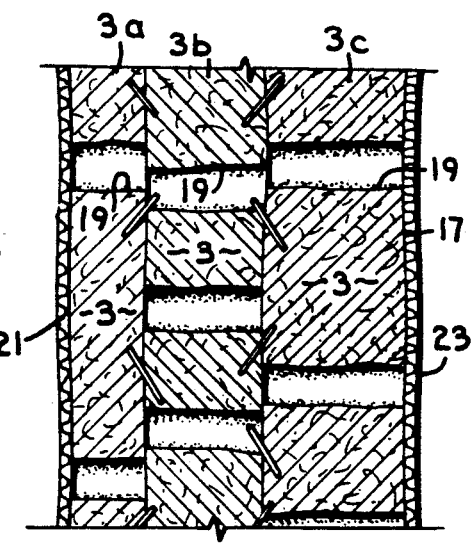
FIG. 6 is an enlarged and fragmentary cross-sectional view of the prosthetic device showing layers having various thicknesses.

The reference number 1 generally refers to a launderable prosthetic device in accordance with the present invention, shown in FIGS. 1 to 6. The prosthetic device 1 comprises a plurality of pads or layers 3. The layers 3 are constructed of a soft, porous, highly resilient, lightweight material which has excellent launderability characteristics, such as a high loft bonded polyester fiber or the like. The material for the layers 3 is preferably spongy and flexible allowing the layers 3 to be compressed, bent, twisted or the like after which the layers 3 have an inherent "memory" which allows the layers 3 to return to an original shape after being deformed by compressing, bending, twisting or the like. Layers 3 having a variety of thicknesses (for example, thin layers 3a, intermediately thick layers 3b, and comparatively thick layers 3c, as shown in FIG. 6) are preferably intermixed to construct the prosthetic device 1 to conform to the complexity of almost any compatibly reasonable surface profile deformity arising from missing body parts as hereinafter described. Preferably, the initial thickness of the various layers 3, utilized to construct the composite layered structure 5 of the prosthetic device 1, as shown in cross-section in FIG. 4, will range between approximately ½ to 1 ½ inch, depending on the application as hereinafter described.

A peripheral edge 7 of each layer 3 is reinforced, such as with an overlock stitch 9 or the like as shown in FIG. 3. As additional reinforcement, a line of straight stitches 10 is sewn along the edge 7 just inside the overlock stitching 9.

The layers 3 are brought into face-to-face abutting relationship with each other, such that they are superimposed one upon the other generally with the wider or layer faces 8 of each layer 3 in face-to-face relationship between adjacent layers 3, and are joined by a basting stitch 11 or the like. The basting stitches 11 are generally inset inwardly from the pad edge 7 approximately ½ to 1 inch or more so that each of the edges 7 are independently easily moved relative to the edges 7 of adjacent abutting layers 3 and thereby providing a more realistic feel than that provided by the prior art. The stitch 11 also lightly connects or tacks the faces 8 together without use of through stitches which allows substantial independent relative movement and flexibility while maintaining the integrity of the device 1.

The total number of layers 3 and the thicknesses thereof depends on the size and shape of the void created by the missing or removed body part. Layers 3 are cut to fit the body region (cavity, depression, area of missing tissue or area to be built up such as where a breast is missing) when stacked on each successive lower layer 3. The layers 3 are added until the size and shape of an inner surface 13 of the composite structure 5 closely approximates the size and shape of a body surface 15 which will receive the prosthesis 1. Similarly, the layering process with the layers 3 stitched into assembled position is continued until an outer surface 17 of the composite structure 5, when slightly compressed as by clothing or the like in its installed configuration, closely approximates the otherwise normal profile lines which would be present, but for the abnormality. Also, sufficient bulk must exist within the composite structure 5 such that the layers 3 cooperate to prevent inward collapse of the prosthetic device 1 and thereby impart to the wearer the desired appearance that is attractive in appearance thereby alleviating the inhibitions and fears of the wearer of being seen in public with such a defect.

For applications where the composite structure 5 has a size or thickness such that greater ventilation must be provided to the boundary between the prosthetic device 1 and the wearer, the layers 3 are configured with randomly spaced apertures, perforations or openings 19 therein. The openings 19 enhance ventilation within the composite structure 5 and promote diffusion of body moisture away from the body surface 15. Further, the openings 19 serve as dead-air spaces to enhance the insulating characteristics of the prosthesis 1. Typically, the dimensions of the openings 19 range between approximately ⅛" to 1 ½" in diameter. The actual size depends on the overall thickness of the composite structure 5 and the relative lateral sizes of the layers 3 which provides effective ventilation for any particular application. The openings 19 can be formed in the layers 3 by stamping or the like.

Interposed between the composite structure 5 and the wearer's body surface 15 is a liner 21. The liner 21 is constructed of a soft, non-abrasive, porous material, such as cotton or the like. Similarly, the outer surface 17 of the layers 3 is covered with a shield cover, layer, or outer enclosure 23 constructed of relatively thin, smooth, porous, durable fabric or material, such as nylon tricot or the like, to provide wear resistance and to facilitate ease of movement of outer clothing relative thereto. Preferably, the material used for the outer enclosure 23 exhibits certain elastic qualities for purposes hereinafter described. Also, preferably, the hue of the outer enclosure 23 approximates the skin color of the wearer in order for the appearance of the prosthetic device 1 to blend with that of the surrounding natural skin.

The peripheral edges of the liner 21 and the outer enclosure 23 are permanently secured together, such as by stitching or the like, such that the composite layered structure 5 is encapsulated in the space therebetween. When so encapsulated, the complimentary edge portions of the liner 21 and the outer enclosure 23 are drawn together such that the elasticity of the outer enclosure 23 partially compresses the pads 3 contained therein to provide a slight outward pressure thereon to approximate the resilience which would exist if the normal body tissue were still present.

An example of an application of the present invention is shown in the embodiment shown in FIGS. 1 to 6 wherein a substantial quantity of body mass is missing from the lower back area of the victim. The prosthetic device 1 is sized and shaped to fill and correct the profile deficiency created thereby. To maintain the desired spacing of the prosthetic device 1, the prosthetic device 1 is secured, by stitching or otherwise, at an appropriate site on the inside of a special garment for support, such as a torso-encircling jacket or vest 25. The vest 25 is preferably constructed of a relatively inelastic net- or mesh-like material which promotes ventilation and which can be worn undetectedly beneath other clothing, such as a shirt 27. The edges of the vest 25 are preferably reinforced, such as by a narrow hem 29 as shown in FIG. 2.

The vest 25 is adapted to facilitate ease of donning and removing same when the wearer 31 is dressing and undressing and in repeatedly positioning the device 1 in its proper position. Similarly, the vest 25 is sufficiently snuggly fitted such that the prosthetic device 1 is inconspicuously maintained in its desired location regardless of the reasonable physical activity or position posed by the wearer 31. Alternatively, the prosthetic device 1 may be secured, by pinning or otherwise, to the inside of a snugly fitted, relatively inelastic undergarment in such a manner that the prosthetic device 1 is held captive inside the undergarment.

Figure 7:
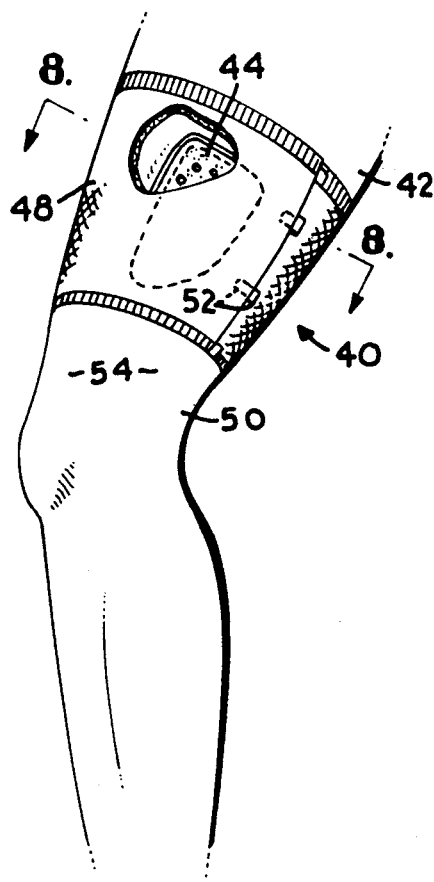
FIG. 7 is a perspective view of a leg of a wearer and a first modified embodiment of a launderable prosthetic device for the leg in accordance with the present invention.
Figure 8:
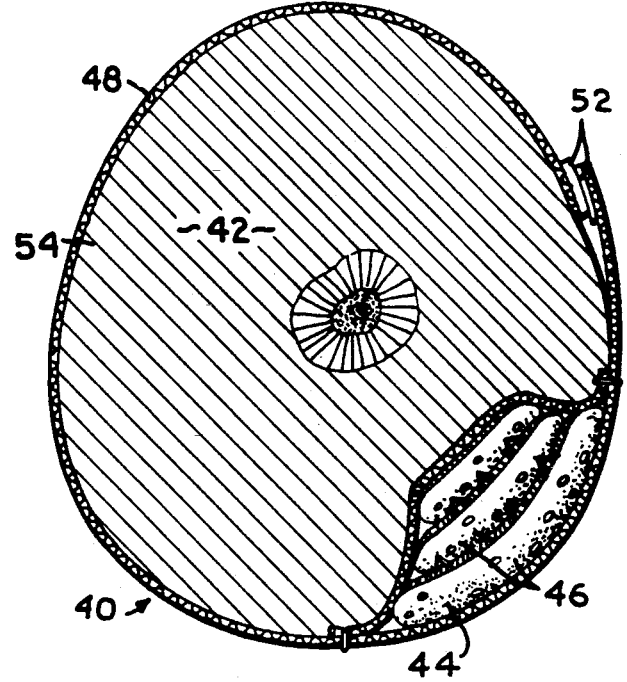
FIG. 8 is an enlarged cross-section view of the leg of the wearer and the first modified prosthetic device, taken along line 8—8 of FIG. 6.

A first modified launderable prosthetic device 40 in accordance with the present invention is shown in FIGS. 7 and 8. Many of the characteristics of the prosthetic device 40 are substantially similar to those already described herein for the device 1 and will not be reiterated here.

In an application of the prosthetic device 40, substantial body mass is missing from a human limb, such as a thigh 42 as shown in FIG. 7. The prosthetic device 40 has a composite structure 44 with a plurality of soft porous layers 46 similar to layers 3 of the previous embodiment except having uniform thickness, as is shown in FIG. 8. The composite structure 44 is secured to a band or sleeve 48 which is adapted to fit about the thigh 42. The band 48 is constructed of a material which grasps the thigh 42 such that it resists downward slippage during physical activity of the wearer 50. The band 48 has opposite mateable ends which are equipped with fasteners 52, such as hook and loop fasteners that are marketed under the tradename Velcro or the like. Alternatively, the band 48 may be constructed of a continuous elastic material and adapted to be telescoped over the wearer's leg 54 to appropriately space the prosthesis 44 as desired; here, however, caution must be observed in order to avoid overly snugging of the band 48 about the leg 54 and thus inhibiting otherwise normal circulation of the leg 54.

A second modified launderable prosthetic device 60 in accordance with the present invention is shown in FIGS. 9 and 10. Many of the characteristics of the second modified prosthetic device 60 are substantially similar to the previously described embodiments and will not be reiterated here.

In an application of the second modified prosthetic device 60 of the present invention, substantial body mass is missing or undeveloped over a substantial portion of a human limb, such as a deformed leg 62 from which substantial subdermal muscle tissue is missing, as is shown in FIG. 9. The prosthetic device 60 comprises a series of pads or layers 64 in a side-by-side abutting relationship.

An innermost layer 66 abuts a liner 68 which, in turn, abuts the leg 62. A next innermost layer 70 has lateral dimensions slightly greater than the lateral dimensions of the innermost layer 66. Similarly, each subsequent layer 64 spaced progressively radially outwardly therefrom has lateral dimensions greater than those of the next radially inward layer 64 abutting thereagainst.

To allow for needed irregularities in the profile of the prosthetic device 60, intermediately sized layers, such as layer 72 referenced in FIG. 10, may be interposed between adjacent layers 74, which substantially span the periphery of the leg 62. With an appropriate intermix of the layers 64 and 72, a naturally formed leg profile can be simulated with the prosthetic device 60.

A first longitudinal terminating edge 76 of each of the layers 64 is gathered together and commonly secured at a first seam 78, such as by stitching or the like. An opposing longitudinal terminating edge 80 of each of the layers 64 is similarly gathered and secured together at a second seam 82. The differences in lateral lengths of the layers 64 as aforesaid are adapted to create a curvature in the composite structure 84 comprising the layers 64 such that the composite structure 84 arches outwardly and thereby naturally cups or curls around the leg 62. A smooth, textured, skin-colored outer layer 85 is integrally secured to the composite structure 84 by stitching to the inner layer 68 so as to form a complete enclosure for the inner layers 64.

A strip fastener means, such as illustrated zipper 86, a hook and loop fastener, or the like, is secured to the seams 78 and 82 for securement of the prosthetic device to the leg 62. The described, vaulted configuration provides a prosthetic device 60 which can be readily and easily donned (and removed) and which reliably maintains its position on and registration with the leg 62 by preventing substantial movement of the prosthetic device 60 relative to the leg 62.

A third modified launderable prosthetic device 90 in accordance with the present invention is shown in FIG. 11. Many of the characteristics of the third modified device 90 are substantially similar to the previously described embodiments and will not be reiterated here.

In an application of the third modified device 90, substantial body mass is missing which would otherwise have a substantially protruding convex curvature, such as a female human breast. The prosthetic device 90 is constructed from a plurality of layers 92. The lateral dimensions of each of the layers 92 is adapted and graduated, whereby an outermost layer 94 has the greatest lateral dimensions. Then, by gathering and securing together of peripheral edges 96 of the successively sized layers 92 into a common seam 98, a composite structure 100 formed by the layers 92 bulges outwardly toward the outermost layer 94 creating the desired size, shape and natural curvature, when partially compressed, which would otherwise by evidenced by the missing breast when confined in a brassiere (not shown). Further, the partial compression is adapted to provide the tactile and deformation qualities of a normal female human breast when so confined.

If the prosthetic device 90 is needed to replace a breast removed during a mastectomy, depending on the radicality of the surgery, additional pads or layers (not shown) simulating a vertical extension, or breast tail, and an underarm extension (both of which are often removed during mastectomy surgery) may be provided and secured to the composite structure.

An inner liner 102 covers an inner surface of the composite structure 100 and an outer shield liner 104 covers the outer convex surface of the composite structure 100. The shield liner 104 and the inner liner 102 are secured together by stitching or the like and enclose the layers 92 and are designed to provide a partial compression of the composite structure 100 as hereinbefore described in order to provide resiliency characteristics to the prosthetic device 90 which closely approximate the look and appearance of the natural female human breast through normally worn clothing.

A fourth modified prosthetic device 110 in accordance with the present invention is shown in FIG. 12. Many of the characteristics of the fourth modified device 10 are substantially similar to the previously described embodiments and will not be reiterated here.

The prosthetic device 110 is constructed of a plurality of pads or layers 112. The lateral dimensions of each of the layers 112 is adapted and graduated, with an outermost layer 114 having the least lateral dimensions of the layers 112, such that the combination of the layers 112 creates a structure having the size, shape and natural curvature of a natural female human breast for confinement in a brassiere (not shown). Peripheral edges 116 of each of the layers 112 are reinforced such as by overlock stitching 118 or the like, and each layer 112, such as layer 120, is secured to its next underlying layer 112, such as layer 122, by stitching 124 or the like.

Alternatively, basting stitches which are confined to adjacent abutting faces of the layers 112 and which are inset from peripheral edges of the layers 112, as hereinbefore described, may be used to maintain the spacing of the layers 112 relative to each other.

The various embodiments provide the ability to construct prosthetic devices not only for substantially planar body regions, such as the chest, stomach, or other parts of the body having relatively flat contours, but also for those regions which have complex convex curvatures.

A common attribute of each of the structures and materials utilized in the aforedescribed embodiments, is the ability to subject each to the hot aqueous solution environments normally and customarily used for ordinary laundering procedures so that the device can be cleaned on a regular basis.

While the preferred material of construction of the prosthesis layers has been described herein as being polyester fiber, it is foreseen that other materials, especially lightweight, flexible and launderable materials, may be alternatively utilized for some embodiments.

It is to be understood that while certain forms of the present invention have been illustrated and described herein, it is not to be limited to the specific forms or arrangement of parts described and shown.

What is claimed and desired to be secured by Letters Patent is as follows:

1. A prosthetic device for restoring a naturally appearing profile of a human body resulting from a missing body part, comprising:
   (a) layering means comprising a plurality of individual pads; each of said pads being constructed of lightweight, resilient and launderable material; each of said pads being sized and shaped to be adapted to form a portion of the missing part; each of said pads being in face-to-face abutment with adjacent pads and being loosely connected thereto by stitching spaced substantially inwardly from peripheral edges of said adjacent pads so as to maintain the position of each of said pads relative to adjacent pads while allowing substantial independent movement of each pad relative to adjacent pads; said pads forming a launderable structure which has the size and shape of the missing part.

2. The device according to claim 1 including:
   (a) containment means for enclosing said layering means; and
   (b) attachment means for securing the device to the body.

3. The prosthetic device according to claim 1 wherein:
   (a) each of said pads is constructed of porous, material and has a reinforced peripheral edge; and
   (b) a first face of each of said pads is secured to a face of an adjacent pad abutting thereagainst by stitching passing through each layer only near the face thereof and substantially inwardly from the peripheral edge thereof.

4. The prosthetic device according to claim 3 wherein:
   (a) said pads are constructed of material ranging in thickness between approximately ½ to 1 ½ inches; and
   (b) said reinforced peripheral edge is an overlock stitch sewn along the periphery of each said pad.

5. The prosthetic device according to claim 3 wherein:
   (a) said material of said layering means is polyester fiber.

6. The prosthetic device according to claim 2 wherein:
   (a) said containment means comprises a relatively thin inner liner constructed of soft, porous, non-abrasive material imposed between said layering means and the body of a wearer; and
   (b) an outer shield liner constructed of smooth, porous material, a peripheral edge of which is secured to a peripheral edge of said inner liner encapsulating said layering means therebetween.

7. The prosthetic device according to claim 2 wherein:
   (a) said attachment means comprises a snug fitting jacket adapted to appropriately position and maintain said prosthetic device relative to said missing body part.

8. The prosthetic device according to claim 3 wherein:
   (a) each successively outward pad of said plurality of pads has progressively greater lateral dimensions; and
   (b) said peripheral edge of each of said pads is secured together causing the composition structure thereof to bulge toward the largest of said pads.

9. A prosthetic device for replacing missing body tissue in a region of the body having a curved surface; comprising:
   (a) a plurality of pads wherein each of said pads is constructed of lightweight, resilient, and launderable material and wherein each of said pads abuts at least one adjacent pads in face-to-face relationship;
   (b) wherein each of said pads is successively laterally wider than each previous pad; and
   (c) each of said pads having laterally spaced opposite sides; each laterally spaced side being secured to associated sides of each of the other pads by loose stitching spaced substantially inwardly from peripheral edges thereof so as to form a bowed construction adapted to correspondingly fit the body curved surface such that the construction replaces the missing body tissue.

10. A prosthetic device adapted to camouflage the existence of missing body tissue on a human body comprising:
    (a) a series of pads constructed of light-weight, porous, resilient, durable, launderable material; each of said pads having relatively uniform thickness; each of said pads having a variety of lateral dimensions; a peripheral edge of each of said pads being reinforced by overlock stitching therealong; each of said pads further reinforced by a series of straight stitches running along and inset radially inward from said overlock stitch;
    (b) said pads being joined in a composite structure comprising said pads spaced in an arrangement adapted to assimilate the size and shape of the missing body tissue and the resiliency of said missing body tissue; each of said pads being positioned relative to the other pads in a fixed configuration and being maintained in said configuration by basting stitches interconnecting a face of each of said pads to a face of another pad abutting thereagainst; said basting stitches substantially inset from said peripheral edges of said pads so as to allow at least partial movement of each of said pads relative to adjacent pads;

(c) an inner liner constructed of soft, flexible, porous material positioned on a portion of said composite structure at a location adapted to abut against a surface of said body;

(d) an outer shield liner constructed of smooth, flexible, porous material surrounding a remaining surface of said composite structure not otherwise covered by said inner liner; a peripheral edge of said shield liner secured to a peripheral edge of said inner liner encapulating said composite structure therebetween; said inner liner and said shield liner being snug about said composite structure so as to partially compress said composite structure; and (e) wherein said prosthetic device is launderable.

11. The prosthetic device according to claim 10 wherein:

(a) said pads are perforated with randomly spaced openings.

12. A method for constructing a human body profile prosthesis for camouflaging a deformity arising from missing body parts, comprising the steps of:

(a) cutting a plurality of appropriately sized pads of lightweight, porous, launderable and resilient material;

(b) reinforcing a peripheral edge of each of said pads;

(c) positioning said pads in face-to-face abutment to each other such that a composite structure is formed by said pads adapted to assimilate the size and shape of the missing body parts;

(d) surface stitching the face of each said pad to the face of each adjoining pad abutting thereagainst;

(e) lining an inner surface of said prosthesis adapted to abut against a wearer thereof with a soft, flexible, launderable, porous inner liner; and (f) covering the outer surface of said prosthesis adapted to abut against the wearer's clothing with a smooth, flexible, launderable, porous outer liner joined to said inner liner.

13. The method for constructing a human body profile prosthesis according to claim 12, including the step of:

(a) perforating one or more of said pads with throughopenings.

14. The method for constructing a human body profile prosthesis according to claim 12 including the step of:

(a) joining said inner and outer liner in such a manner so as to slightly compress said pads therebetween such that a pressure is continuously exerted against said liners by said pads during use.

15. The method for constructing a human body profile prosthesis according to claim 12, including the steps of:

(a) sizing said plurality of pads such that each pad situated radially outward from an innermost pad has progressively larger lateral dimensions; and (b) stitching opposite edges of said pads into a common seam such that the composite structure thereof bulges outwardly toward the pad having the largest lateral dimensions.

* * * * *